United States Patent [19]
Rao et al.

[11] Patent Number: 5,365,010
[45] Date of Patent: * Nov. 15, 1994

[54] METHOD FOR REGENERATING LEWIS ACID-PROMOTED TRANSITION ALUMINA CATALYSTS USED FOR ISOPARAFFIN ALKYLATION BY CALCINATION

[75] Inventors: Pradip Rao, San Jose; David L. King, Mountain View; Michael D. Cooper, San Jose; Jerome E. Say, Rancho Palos Verdes, all of Calif.

[73] Assignee: Catalytica, Inc., Mountain View, Calif.

[*] Notice: The portion of the term of this patent subsequent to Oct. 20, 2009 has been disclaimed.

[21] Appl. No.: 718,394

[22] Filed: Jun. 20, 1991

Related U.S. Application Data

[63] Continuation-in-part of Ser. No. 588,448, Sep. 26, 1990, abandoned, Ser. No. 697,318, May 7, 1991, Pat. No. 5,157,197, and Ser. No. 697,320, May 7, 1991, abandoned.

[51] Int. Cl.⁵ ............... C07C 2/58; B01J 20/34; B01J 38/12
[52] U.S. Cl. ........................ 585/726; 585/721; 585/727; 585/728; 585/906; 502/38
[58] Field of Search .............. 502/38; 585/726, 727, 585/728, 721, 906

[56] References Cited

U.S. PATENT DOCUMENTS

| | | | |
|---|---|---|---|
| 2,288,484 | 6/1942 | Rearick | 502/38 |
| 2,405,565 | 8/1946 | Fawcett et al. | |
| 2,406,869 | 9/1946 | Upham | 252/211 |
| 2,748,090 | 5/1956 | Watkins | 502/203 |
| 2,804,491 | 8/1957 | May et al. | 585/726 |
| 2,824,146 | 2/1958 | Kelly et al. | 585/465 |
| 2,824,150 | 2/1958 | Knight et al. | 585/465 |
| 2,824,151 | 2/1958 | Kelly et al. | 585/465 |
| 2,824,152 | 2/1958 | Knight et al. | 585/465 |
| 2,824,153 | 2/1958 | Kelly et al. | 585/465 |
| 2,824,154 | 2/1958 | Knight et al. | 585/465 |
| 2,824,155 | 2/1958 | Knight et al. | 585/726 |
| 2,824,156 | 2/1958 | Knight et al. | 585/465 |
| 2,824,157 | 2/1958 | Knight et al. | 585/465 |
| 2,824,158 | 2/1958 | Kelly et al. | 585/465 |
| 2,824,159 | 2/1958 | Kelly et al. | 585/465 |
| 2,824,160 | 2/1958 | Knight et al. | 585/465 |
| 2,824,161 | 2/1958 | Knight et al. | 585/465 |
| 2,824,162 | 2/1958 | Knight et al. | 585/465 |

(List continued on next page.)

FOREIGN PATENT DOCUMENTS

| | | |
|---|---|---|
| 1346135 | 1/1963 | France . |
| 2504121 | 10/1982 | France . |
| 614079 | 2/1974 | U.S.S.R. . |
| WO90/00533 | 1/1990 | WIPO . |
| WO90/00534 | 1/1990 | WIPO . |

OTHER PUBLICATIONS

Yagubov, Kh. M. et al., *Azerb. Khim. Sh.*, (1984) 5:58.
Kozorezov, Yu, et al., *Zh. Print. Khim.* (Leningrad), (1984) 57(12):2681–4.
Kozorezov, Yu. I., *Neftekhimiya* (1977) 17:(3):396–400; abstract only.

*Primary Examiner*—Anthony McFarlane
*Assistant Examiner*—E. D. Irzinski
*Attorney, Agent, or Firm*—Morrison & Foerster

[57] ABSTRACT

This invention is a process for the regeneration of a catalyst system component comprising certain transition aluminas promoted with a Lewis acid (preferably BF₃) which have been used in the alkylation of isoparaffin with olefins. The process involves the calcination of the catalyst system component to volatilize and to oxidize the reaction product residue adhering to the solid catalyst. The process may include recovery and recycle of the involved Lewis acid.

21 Claims, 2 Drawing Sheets

5,365,010
Page 2

U.S. PATENT DOCUMENTS

| | | | |
|---|---|---|---|
| 2,939,890 | 6/1960 | Hervert et al. | 502/203 |
| 2,945,907 | 7/1960 | Knight et al. | 585/726 |
| 2,976,338 | 3/1961 | Thomas | 585/525 |
| 3,054,835 | 9/1962 | Hervert et al. | 260/671 |
| 3,054,836 | 9/1962 | Hervert et al. | 260/671 |
| 3,068,301 | 12/1962 | Hervert et al. | 585/463 |
| 3,114,785 | 12/1963 | Hervert et al. | 585/669 |
| 3,217,062 | 11/1965 | Hervert et al. | 260/683.2 |
| 3,217,063 | 11/1965 | Hervert et al. | 260/683.2 |
| 3,220,958 | 11/1965 | Hervert et al. | 252/433 |
| 3,433,747 | 3/1969 | Magee et al. | 252/433 |
| 3,647,916 | 3/1972 | Ceasar et al. | 585/722 |
| 3,833,679 | 9/1974 | Gardner et al. | 585/749 |
| 3,851,004 | 11/1974 | Yang | 585/467 |
| 3,893,942 | 7/1975 | Yang | 585/722 |
| 4,058,575 | 11/1977 | Cahn et al. | 585/374 |
| 4,308,414 | 12/1981 | Madgavkar et al. | 585/525 |
| 4,407,731 | 10/1983 | Imai | 502/203 |
| 4,427,791 | 1/1984 | Miale et al. | 502/203 |
| 4,751,341 | 6/1988 | Rodewald | 585/533 |
| 4,774,364 | 9/1988 | Chou | 568/697 |
| 4,914,256 | 4/1990 | Rodewald | 585/726 |
| 4,918,255 | 4/1990 | Chou et al | 585/331 |
| 4,935,577 | 6/1990 | Huss, Jr. et al. | 585/726 |
| 4,956,518 | 9/1990 | Child et al. | 585/726 |
| 4,992,614 | 2/1991 | Rodewald | 585/722 |
| 4,992,616 | 2/1991 | Chou et al. | 585/723 |
| 5,157,197 | 10/1992 | Cooper et al. | 585/726 |

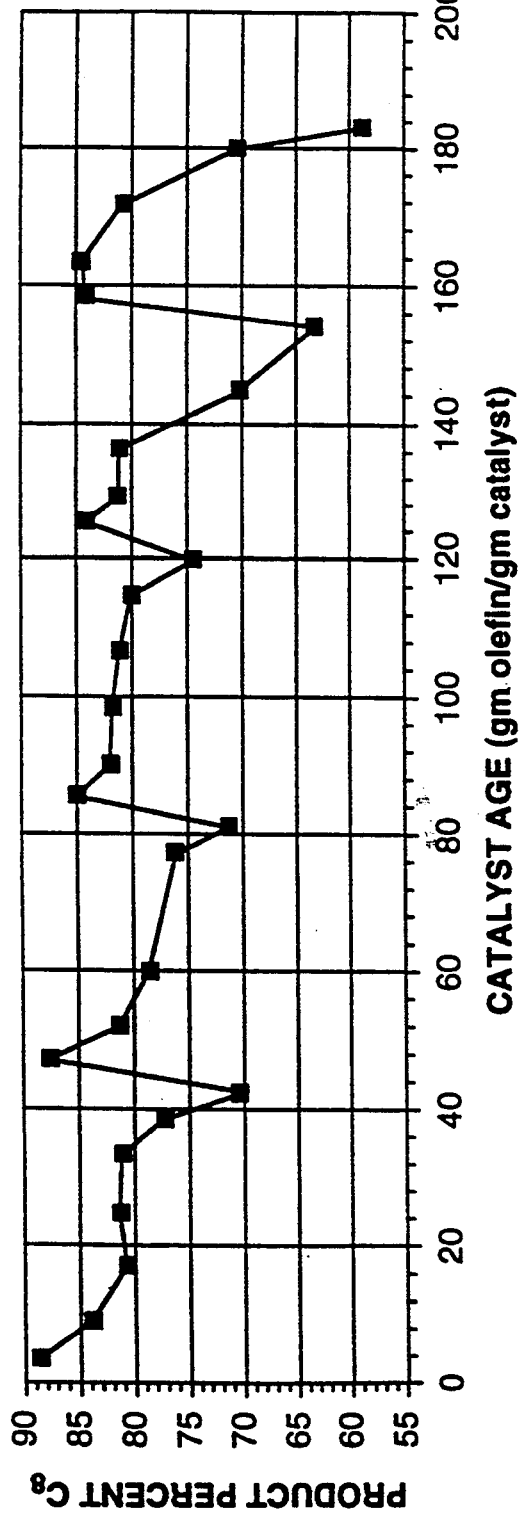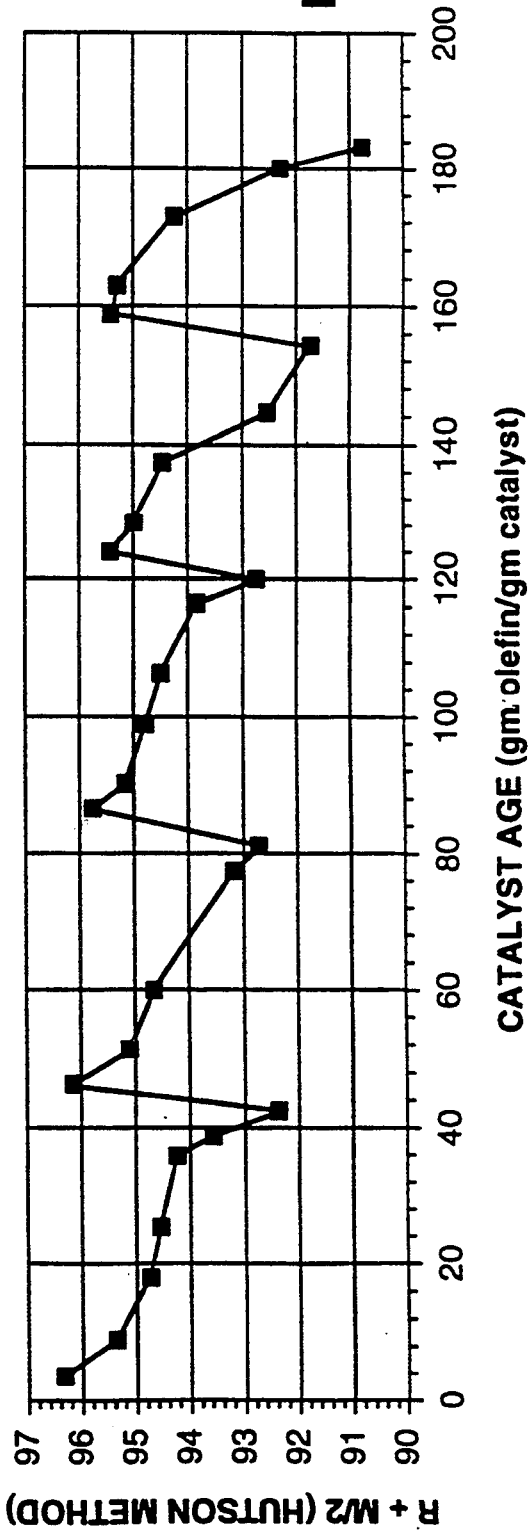

METHOD FOR REGENERATING LEWIS ACID-PROMOTED TRANSITION ALUMINA CATALYSTS USED FOR ISOPARAFFIN ALKYLATION BY CALCINATION

RELATED APPLICATIONS

This is a continuation-in-part of U.S. patent application Nos. 07/588,448 to Cooper et al. entitled "ISOPARAFFIN ALKYLATION USING A LEWIS ACID PROMOTED TRANSITION ALUMINA CATALYST filed Sep. 26, 1990 now abandoned; 07/697,318 to Cooper et al. entitled "ISOPARAFFIN ALKYLATION USING A LEWIS ACID PROMOTED TRANSITION ALUMINA CATALYST filed May 7, 1991; now U.S. Pat. No. 5,157,197; and 07/697,320 to Cooper et al. entitled "LEWIS ACID PROMOTED TRANSITION ALUMINA CATALYSTS SUITABLE FOR ISOPARAFFIN ALKYLATION filed May 7, 1991, and now abandoned; the entirety of which are incorporated by reference.

FIELD OF THE INVENTION

This invention is a process for the regeneration of a catalyst system component comprising certain transition aluminas promoted with a Lewis acid (preferably $BF_3$) which have been used in the alkylation of isoparaffin with olefins. The process involves the calcination of the catalyst system component to volatilize and to oxidize the reaction product residue adhering to the solid catalyst. The process may include recovery and recycle of the involved Lewis acid.

BACKGROUND OF THE INVENTION

The preparation of high octane blending components for motor fuels using strong acid alkylation processes (notably where the acid is hydrofluoric acid or sulfuric acid) is well-known. Alkylation is the reaction in which an alkyl group is added to an organic molecule (typically an aromatic or olefin). For production of gasoline blending stocks, the reaction is between an isoparaffin and an olefin. Alkylation processes have been in wide use since World War II when high octane gasolines were needed to satisfy demands from high compression ratio or supercharged aircraft engines. The early alkylation units were built in conjunction with fluid catalytic cracking units to take advantage of the light end by-products of the cracking units: isoparaffins and olefins. Fluidized catalytic cracking units still constitute the major source of feedstocks for gasoline alkylation units. In spite of the mature state of strong acid alkylation technology, existing problems with the hydrofluoric and sulfuric acid technologies continue to be severe: disposal of the used acid, unintentional emission of the acids during use or storage, substantial corrosivity of the acid catalyst systems, and other environmental concerns.

Although a practical alkylation process using solid acid catalysts having little or no corrosive components has long been a goal, commercially viable processes do not exist.

The open literature shows several systems used to alkylate various hydrocarbon feedstocks.

The American Oil Company obtained a series of patents in the mid-1950's on alkylation processes involving Cbd 2–$C_{12}$ (preferably $C_2$ or $C_3$) olefins and $C_4$–$C_8$ isoparaffins. The catalysts used were $BF_3$-treated solids and the catalyst system (as used in the alkylation process) also contained free $BF_3$. A summary of those patents is found in the following list:

| U.S. Pat. No. | Inventor | $BF_3$-Treated Catalyst* (with free $BF_3$) |
|---|---|---|
| 2,804,491 | Kelly et al. | $SiO_2$ stabilized $Al_2O_3$ (10%–60% by weight $BF_3$) |
| 2,824,146 | Kelly et al. | metal pyrophosphate hydrate |
| 2,824,150 | Knight et al. | metal sulfate hydrate |
| 2,824,151 | Kelly et al. | metal stannate hydrate |
| 2,824,152 | Knight et al. | metal silicate hydrate |
| 2,824,152 | Kelly et al. | metal orthophosphate hydrate |
| 2,824,154 | Knight et al. | metal tripolyphosphate hydrate |
| 2,824,155 | Knight et al. | metal pyroarsenate hydrate |
| 2,824,156 | Kelly et al. | Co or Mg arsenate hydrate |
| 2,824,157 | Knight et al. | Co, Al or Ni borate hydrate |
| 2,824,158 | Kelly et al. | metal pyroantimonate hydrate salt |
| 2,824,159 | Kelly et al. | Co or Fe molybdate hydrate |
| 2,824,160 | Knight et al. | Al, Co, or Ni tungstate hydrate |
| 2,824,161 | Knight et al. | borotungstic acid hydrate or Ni or Cd borotungstate hydrate |
| 2,824,162 | Knight et al. | phosphomolybdic acid hydrate |
| 2,945,907 | Knight et al. | solid gel alumina (5%–100% by weight of Zn or Cu fluoborate, preferably anhydrous |

*may be supported on $Al_2O_3$

None of these disclose a process for alkylating olefins and isoparaffins using neat alumina treated with $BF_3$ nor a calcination process for regenerating the catalyst.

Related catalysts have been used to oligomerize olefins. U.S. Pat. No. 2,748,090 to Watkins suggests the use of a catalyst made up of a Group VIII metal (preferably nickel), a phosphoric acid (preferably containing phosphorus pentoxide), placed on an alumina adsorbent, and pretreated with $BF_3$. Alkylation of aromatics is suggested.

U.S. Pat. No. 2,976,338 to Thomas suggests a polymerization catalyst comprising a complex of $BF_3$ or $H_3PO_4$ optionally on an adsorbent (such as activated carbon) or a molecular sieve optionally containing potassium acid fluoride.

Certain references suggest the use of alumina-containing catalysts for alkylation of aromatic compounds. U.S. Pat. No. 3,068,301 to Hervert et al. suggests a catalyst for alkylating aromatics using "olefin-acting compounds". The catalyst is a solid, silica-stabilized alumina up to 10% $SiO_2$, all of which has been modified with up to 100% of weight $BF_3$. None of the prior references suggest a process nor the material used in the processes disclosed here.

Other $BF_3$-treated aluminas are known. For instance, U.S. Pat. No. 3,114,785 to Hervert et al. suggests the use of a $BF_3$-modified, substantially anhydrous alumina to shift the double bond of 1-butene to produce 2-butene. The preferred alumina is substantially anhydrous gamma-alumina, eta-alumina, or theta-alumina. The various aluminas will adsorb or complex with up to about 19% by weight fluorine depending upon the type of alumina and the temperature of treatment. Hervert et al. does not suggest using these catalysts in alkylation reactions.

In U.S. Pat. No. 4,407,731 to Imai a high surface area metal oxide such as alumina (particularly gamma-alumina, eta-alumina, theta-alumina, silica, or a silica-alumina) is used as a base or support for $BF_3$. The $BF_3$ treated metal oxide is used for generic oligomerization and alkylation reactions. The metal oxide is treated in a complicated fashion prior to being treated with $BF_3$. The first step entails treating the metal oxide with an acid solution and with a basic aqueous solution. The support is washed with an aqueous decomposable salt such as ammonium nitrate. The support is washed using deionized H₂O until the wash water shows no alkali or alkaline earth metal cations in the filtrate. The support is dried and calcined. The disclosure suggests generically that BF₃ is then introduced to the treated metal oxide support. The examples show introduction of the BF₃ at elevated temperatures, e.g, 300° C. or 350° C.

Similarly, U.S. Pat. No. 4,427,791 to Miale et 91. suggests the enhancement of the acid catalytic activity of inorganic oxide materials (such as alumina or gallia) by contacting the material with ammonium fluoride or boron fluoride, contacting the treated inorganic oxide with an aqueous ammonium hydroxide or salt solution, and calcining the resulting material. The inorganic oxides treated in this way are said to exhibit enhanced Brönsted acidity and, therefore, is said to have improved acid activity towards the catalysis of numerous and several reactions (such as alkylation and isomerization of various hydrocarbon compounds). A specific suggested use for the treated inorganic oxide is as a matrix or support for various zeolite materials ultimately used in acid catalyzed organic compound conversion processes.

U.S. Pat. No. 4,751,341 to Rodewald shows a process for treating a ZSM-5 type zeolite with BF₃ to reduce its pore size, enhance its shape selectivity, and increase its activity towards the reaction of oligomerizing olefins. The patent also suggests using these materials for alkylation of aromatic compounds.

Certain Soviet publications suggest the use of Al₂O₃ catalysts for alkylation processes. Benzene alkylation using those catalysts (with 3 ppm to 5 ppm water and periodic additions of BF₃) is shown in Yagubov, Kh. M. et al., *Azerb. Khim. Zh.*, 1984, (5) p. 58. Similarly, Kozorezov, Yu and Levitskii, E. A., *Zh. Print. Khim. (Leningrad)*, 1984, 57 (12), p. 2681, show the use of alumina which has been treated at relatively high temperatures and modified with BF₃ at 100° C. There are no indications that BF₃ is maintained in excess. Isobutane alkylation using Al₂O₃/BF₃ catalysts is suggested in *Neftekhimiya*, 1977, 17 (3), p. 396; 1979, 19 (3), P. 385. The olefin is ethylene. There is no indication that BF₃ is maintained in excess during the reaction. The crystalline form of the alumina is not described.

U.S. Pat. No. 4,918,255 to Chou et al. suggests a process for the alkylation of isoparaffins and olefins using a composite described as "comprising a Lewis acid and a large pore zeolite and/or a non-zeolitic inorganic oxide". The process disclosed requires isomerization of the olefin feed to reduce substantially the content of alpha-olefin and further suggests that water addition to the alkylation process improves the operation of the process. The best Research Octane Number (RON) product made using the inorganic oxides (in particular SiO₂) is shown in Table 6 to be 94.0.

U.S. Pat. No. 4,992,616 to Chou et al. deals with the process noted above for alkylation of isoparaffins and olefins using a composite described as "comprising a Lewis acid and a large pore zeolite" but requiring water addition for improvement the operation of the process. The best Research Octane Number (RON) product shown in the examples and made using the disclosed invention is 86.0 (Table 2).

Similarly, PCT published applications WO 90/00533 and 90/00534 (which are based in part on the U.S. patent to Chou et al. noted above) suggest the same process as does Chou et al. WO 90/00534 is specific to a process using boron trifluoride-treated inorganic oxides including "alumina, silica, boria, oxides of phosphorus, titanium oxide, zirconium oxide, chromia, zinc oxide, magnesia, calcium oxide, silica-alumina-zirconia, chromia-alumina, alumina-boria, silica-zirconia, and the various naturally occurring inorganic oxides of various states of purity such as bauxite, clay and diatomaceous earth". Of special note is the statement that the "preferred inorganic oxides are amorphous silicon dioxide and aluminum oxide". The examples show the use of amorphous silica (and BF₃) to produce alkylates having an RON of no greater than 94.

U.S. Pat. No. 4,935,577 to Huss, Jr. et al. teaches a process for the catalytic distillation of various hydrocarbons by e.g., alkylation or oligomerization, using a catalyst "consisting essentially of a Lewis acid promoted inorganic oxide." The inorganic oxide may be selected from the non-zeolitic materials discussed above with regard to the Chou et al. published PCT applications. Additionally, the inorganic oxide may be a large pore crystalline molecular sieve. The best exemplified alkylate appeared to have an RON value of 93 (Table 2).

None of these disclosures show the alkylation of isoparaffins and olefins using crystalline transition aluminas promoted with Lewis acids for the production of high octane gasoline blending components.

There are a variety of disclosed ways to regenerate catalysts used in alkylation processes or using Lewis acids. Typical of such processes are the following.

U.S. Pat. No. 3,647,916, to Caesar St al. shows a process for isoparaffinolefin alkylation using crystallatine zeolite catalysts at low isoparaffin to olefin ratios. The zeolite is first steamed to reduce the number of acid sites and so reduce the amount of olefin polymerization which occurs. The isoparaffin is added to the catalyst before the olefin is introduced to further limit the amount of polymerization. There is no discussion of the use of auxiliary Lewis acids in conjunction with the zeolites. Nevertheless, the catalysts are susceptible to deactivation due to the "accumulation in the pores thereof of olefin polymerization products". The regeneration is carried out by burning the surface residue "in an oxygen-containing atmosphere at an elevated temperature in the range of about 800° to 1400° F. followed by a step in which the catalyst is contacted with an aromatic or polar solvent.

U.S. Pat. No. 3,833,679 to Gardner et al. shows a paraffin isomerization process using an HSbF₆ catalyst supported on a fluorided alumina. The catalyst was regenerated by introduction of an HF stream sufficient to convert to any SbF₅ to HSbF₆. No mention is made of removal of any hydrocarbonaceous materials from the catalyst using this treatment.

U.S. Pat. No. 3,893,942 to Yang also shows a process for isoparaffin-olefin alkylation using crystallatine zeolite catalysts. A small amount of a hydrogenation catalyst (Group VIII metal) is included in the zeolite. Hydrogen gas is periodically introduced into the zeolite (apparently after the catalyst has been partially deactivated) and restores the activity of the catalyst. Yang indicates that the nature of the chemical reaction between the hydrocarbonaceous deposit and the hydrogen is not clear but hydrogen is consumed and the alkylation activity is restored. This procedure is said to avoid "refractory coke deposits" formed when using high temperature inert gas regeneration treatments. Oxidative treatments are then said to be necessary. A paraffinic wash is desirably first applied to the catalyst to assist in the following hydrogenation step.

U.S. Pat. No. 3,855,343 to Huang et al. teaches an isoparaffin-olefin alkylation process in which the catalyst is a combination of a macroreticular acid cation exchange resin and boron trifluoride. The boron trifluoride is present in an amount in excess of that needed to saturate the resin. This catalyst is said to "age" and after some period of time must be regenerated. The catalyst is regenerated by solvent extraction with a polar solvent, preferably a low molecular weight alcohol.

The process disclosed in U.S. Pat. No. 4,058,575 to Cahn et al. is a method of converting hydrocarbons, e.g., by alkylating them, in the presence of a Lewis acid and a strong Bronsted acid. Partially deactivated catalytic materials are pretreated with a hydrocarbon to remove contaminants and deactivated catlayst species.

The U.S. Pat. No. 4,308,414 to Madgavkar shows a process for oligomerizing longer alpha-olefins using a particulate adsorbent (preferably $SiO_2$) and adsorbed boron trifluoride and water. The catalyst is regenerated by the procedure of adding a small amount of water with the feed olefin.

The U.S. Patent Nos. 4,914,256 and 4,992,614 to Rodewald suggest the reactivation of catalysts (particularly supported boron trifluoride-containing alkylation catalysts) used in a variety of hydrocarbon conversion catalysts by application of ultrasonic energy to the partially deactivated catalyst. The process is said to eliminate the need for separation of the catalyst from the feedstock nor to subject the catalyst to a "burn-off" operation.

These disclosures do not show the use of a lower temperature calcination to revive a catalyst system component comprising certain transition aluminas which are promoted with a Lewis acid (preferably $BF_3$) and which have been used in the alkylation of isoparaffin with olefins and which calcination preserves the crystalline structure of the aluminas.

SUMMARY OF THE INVENTION

This invention is a process for the regeneration of a catalyst system component comprising certain transition aluminas promoted with a Lewis acid (preferably $BF_3$) which have been used in the alkylation of isoparaffin with olefins. The process involves the calcination of the catalyst system component to volatilize and to oxidize the reaction product residue adhering to the solid catalyst. The process may include recovery and recycle of the involved Lewis acid.

The alkylation process in which these catalysts are used produces alkylates suitable for use as very high octane, non-aromatic blending components in motor fuels. The alkylates are produced from olefins and isoparaffins. The catalyst used comprises one or more transitional aluminas which are treated with at least one Lewis acid, preferably $BF_3$. The process optimally utilizes a minor amount of free Lewis acid and produces high octane alkylate at a variety of reaction temperatures between $-30°$ C. and $40°$ C.

The regeneration process includes the steps of separating the alumina component from the reaction medium and heating the alumina in the presence of an oxygen-bearing gas to a temperature between $350°$ C. and $800°$ C., preferably between $450°$ and $700°$ C., and most preferably between $500°$ and $650°$ C. A step conducted at a lower temperature involving the volatilization of certain hydrocarbons and recovering the Lewis acid may be included if so desired.

BRIEF DESCRIPTION OF THE DRAWINGS

FIGS. 2A and 2B are also graphs showing the efficacy of a sample of the catalyst over several calcination regenerations but using a typical refinery feedstock.

DESCRIPTION OF THE INVENTION

Figure 1A:
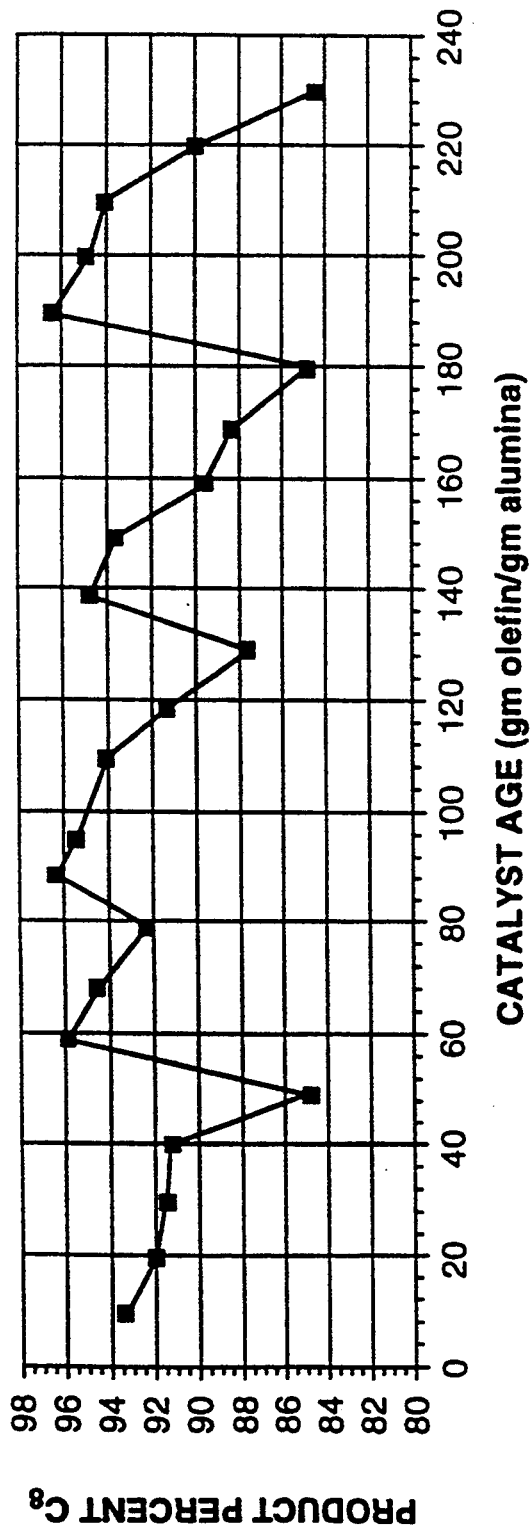
FIGS. 1A and 1B are graphs showing the efficacy of a sample of the catalyst over several calcination regenerations while using a laboratory accelerated aging technique.

This invention is a process for regenerating the component of a catalyst system which has been used for producing alkylate products from olefins and isoparaffins. The catalyst system itself comprises certain transition aluminas which have been treated with one or more Lewis acids in combination with a minor amount of free Lewis acid.

The alumina catalyst component of this invention is made by contacting free Lewis acid with certain transition alumina substrates.

The Alumina Catalyst Component

The alumina catalyst component comprises or consists essentially of a major amount of transition aluminas (preferably eta- or gamma-alumina) which has been treated with a Lewis acid, preferably $BF_3$. The catalyst component is acidic in nature and contains substantially no metals (except, of course, aluminum and the semimetal boron) in catalytic amounts except as may be present in trace amounts in the $BF_3$ or alumina.

Alumina

Aluminum oxide (alumina) occurs abundantly in nature, usually in the form of a hydroxide in the mineral bauxite, along with other oxidic impurities such as $TiO_2$, $Fe_2O_3$, and $SiO_2$. The Bayer process is used to produce a reasonably pure $Al_2O_3$ having a minor amount of $Na_2O$. The Bayer process $Al_2O_3$ is further treated to produce a variety of alumina hydroxides:

| Material | Common Name | % $H_2O$ | $H_2O/Al_2O_3$ | CAS Index No. |
| --- | --- | --- | --- | --- |
| α-trihydrate | hygrargillite/gibbsite | 35 | 3.0 | 14762-493 |
| β-trihydrate | bayerite | 35 | 3.0 | 20257-20-9 or 12252-72-1 |
| β-trihydrate | nordstrandite | 35 | 3.0 | 13840-05-6 |
| α-monohydrate | boehmite | 15 | 1.0 | 1318-23-6 |
| hydrate | psuedoboehmite | 26 | 2.0 | — |

The aluminum hydroxides may then be treated by heating to produce various activated or transition aluminas. For instance, the aluminum hydroxide known as boehmite may be heated to form a sequence of transition phase aluminas: gamma, delta, theta, and finally, alpha (see Wefers et al., "Oxides and Hydroxides of Alumina", Technical Paper No. 19, Aluminum Company of America, Pittsburgh, Pa., 1972, pp.1-51). Transition aluminas (and their crystalline forms) include:

| | |
| --- | --- |
| gamma | tetragonal |
| delta | orthorhombic/tetragonal |
| eta | cubic |
| theta | monoclinic |
| chi | cubic/hexagonal |

| kappa | hexagonal |
| lambda | orthorhombic |

Activated aluminas and aluminum hydroxides are used in various chemical processes as catalyst and adsorbents.

The aluminas suitable for use in this process include the noted transition aluminas: gamma, delta, eta, theta, chi, kappa rho, or lambda. Especially preferred are gamma- and eta-aluminas. Mixtures of the two are also desireable.

Since it is difficult to produce a substantially pure single phase transition alumina, mixtures of various aluminas are tolerable so long as a major amount of the specified alumina is present in the catalyst. For instance, in the production of eta-alumina, gamma-alumina is often concurrently present in the resulting product. Indeed, x-ray diffraction analysis can only difficultly detect the difference between the two phases. Aluminum hydroxides (boehmite, gibbsite, etc.) may be present in the predominately transition phase product in more than trivial amounts so long as they do not substantially affect the desired alkylation reaction.

The alumina may be produced in any appropriate form such as pellet, granules, bead, sphere, powder, or other shape to facilitate its use in fixed beds, moving beds, or fluidized beds.

Lewis Acids

The catalyst system used in this process uses one or more Lewis acids in conjunction with the alumina noted above.

A Lewis acid is a molecule which can form another molecule or an ion by forming a complex in which it accepts two electrons from a second molecule or ion. Typical strong Lewis acids include boron halides such as $BF_3$, $BCl_3$, $BBr_3$, and $BI_3$; antimony pentachloride ($SbF_5$); aluminum halides ($AlCl_3$ and $AlBr_3$); titanium halides such as $TiBr_4$, $TiCl_4$, and $TiCl_3$; zirconium tetrachloride ($ZrCl_4$); phosphorus pentafluoride ($PF_5$); iron halides such as $FCl_3$ and $FeBr_3$; and the like. Weaker Lewis acids such as tin, indium, bismuth, zinc, or mercury halides are also acceptable. Preferred Lewis acids are $SbF_5$, $AlCl_3$, and $BF_3$; most preferred is $BF_3$.

Catalyst Preparation

The catalyst system may be prepared in situ in the alkylation reactor by passing the Lewis acid in gaseous form through the vessel containing the transition alumina. Alternatively, the alumina may be contacted with the Lewis acid and later introduced into the reactor, In any case, the alumina must be substantially dry prior to contact with the Lewis acid and maintained substantially dry. Contact temperatures between $-25°$ C. and about $100°$ C. are acceptable; a temperature between $-25°$ C. and $30°$ C. is preferred. The partial pressure of gaseous Lewis acid added to the alumina is not particularly important so long as a sufficient amount of Lewis acid is added to the alumina. We have found that treatment of the alumina with $BF_3$ at the noted temperatures will result in an alumina-$BF_3$ complex containing $BF_3$ sufficient to carry out the alkylation. The alumina contains between 0.5% and 30% by weight of $BF_3$.

Obviously, the alumina may be incorporated into a binder prior to its treatment with Lewis acid. The binders may be clays (such as montmorillonite and kaolin) or silica based materials (such as gels or other gelatinous precipitates). Other binder materials include carbon and metal oxides such as alumina, silica, titania, zirconia, and mixtures of those metal oxides. The composition of the binders is not particularly critical but care must be taken that they not substantially interfere with the operation of the alkylation reaction.

The preferred method for incorporating the catalytic alumina into the binder is by mixing an aluminum hydroxide precursor (such as boehmite) with the binder precursor, forming the desired shape, and calcining at a temperature which both converts the aluminum hydroxide precursor into the appropriate transition phase and causes the binder precursor to bind the alumina particles. The absolute upper temperature limit for this calcination is about $1150°$ C. Temperatures below about $1000°$ C. are appropriate.

Because of the desirability of using a slurry reactor and maximizing surface area, the most desired form of the catalyst is a powder of neat transition alumina sized appropriately for the slurry reactor system employed.

Alkylation Process

The alkylation process involves contacting an isoparaffin with an olefin in the presence of the catalyst discussed above and in the presence of a minor amount of free Lewis acid.

Specifically, the catalyst of this invention is active at low temperatures (as low as $-30°$ C.) as well as at higher temperatures (nearing $50°$ C.). Lower temperatures ($-5°$ C. to $15°$ C.) are preferred because of the enhanced octane of the alkylate produced and are particularly preferred if the feedstream contains more than about 1% isobutylene. Higher temperatures also tend to produce larger amounts of polymeric materials.

The pressure used in this process is not particularly critical. In general, the pressure must be kept high enough to maintain the reactants and products in the liquid phase, although the catalyst will produce alkylation products when the feedstock is gaseous. As a practical guideline, the process may be operated at atmospheric pressure to about 750 psig. Higher pressures within the range allow recovery of excess reactants by flashing after the product stream leaves the alkylation reactor.

The amount of catalyst used in this process depends upon a wide variety of disparate variables. Nevertheless, we have found that the Weight Hourly Space Velocity ("WHSV"=weight of olefin feed/hour÷weight of catalyst) may effectively be between 0.1 and 120, especially between 0.5 and 30. The overall molar ratio of paraffin to olefin is between about 1.0 and 50.0. Preferred ranges include 2.0 and 25.0; the more preferred include 3.0 and 12.0.

The feedstreams introduced into the catalyst desirably comprise isoparaffins having from four to ten carbon atoms and, most preferably, four to six carbon atoms. Isobutane is most preferred because of its ability to make high octane alkylate. The olefins desirably contain from three to five carbon atoms, i.e., propylene, cis- and trans-butene-2, butene-1, and amylenes. Preferably, the olefin stream contains little (if any) isobutylene. Similarly, for the inventive catalysts, the process works better in producing high octane alkylate if the feedstream contains little or no butadiene (preferably less than 0.2% to 0.3% molar of the total feedstream) and a minimal amount of isobutylene, e.g., less than about 2.5% molar. Similarly the butene-1 content should be minimized.

The products of this alkylation process typically contain a complex mixture of highly branched alkanes. For instance, when using isobutane as the alkane and n-butylene as the olefin, a mixture of 2,2,3-; 2,2,4-; 2,3,3-; and 2,3,4-trimethylpentane (TMP) will result often with minor amounts of other isomeric or polymeric products. The 2,3,4-TMP isomer is the lowest octane isomer of the noted set. The 2,2,3- and 2,2,4-TMP isomers are higher octane components. Calculated average octane values (RON plus Motor Octane Number/2) of the various $C_8$ isomers are:

| Isomer | Octane (R + M)/2 |
| --- | --- |
| 2,2,3- | 104.80 |
| 2,2,4- | 100.00 |
| 2,3,3- | 102.08 |
| 2,3,4- | 99.30 |

Clearly an alkylation process using the noted feedstocks should maximize $C_8$ production, minimize the 2,3,4-TMP isomer, $C_7$ isomers, and $C_{12}$+fraction while maximizing 2,2,3- and 2,3,3-TMP isomers.

The process (in addition to being capable of sustaining the temperatures noted above) can be carried out in the liquid, vapor, or mixed liquid and vapor phase. Liquid phase operation is preferred in this process.

The process involved may utilize the catalyst in a fixed bed using single or multiple feeds. That is to say, the feedstocks may be independently introduced at one or more points throughout the bed or between multiple beds. Desirably, the catalyst is contacted with the feedstocks in one or more of continuously stirred reactors, preferably with feed to each reactor.

We have found that addition of water or alcohols to the alkylation step does not produce improvement in the alkylate produced.

Regeneration Step

As we have discussed above, this process involves the steps of separating the solid catalytic material from the alkylate by a liquid-solid separation technique and heating the alumina component in the presence of an oxygen-containing gas. The alumina is desirably first contacted with an inert gas to strip excess gaseous Lewis acid and light hydrocarbons from the solid alumina component. The alumina may also be treated with a mild heating step prior to the high temperature heating step to further strip hydrocarbons from the alumina. The hydrocarbons and Lewis acid may be recycled as appropriate.

The higher temperature oxidation step is typically carried out in the presence of an oxygen-containing gas, e.g., air, oxygen-enriched air, oxygen, etc. Care must be taken to control the localized temperatures within the catalyst mass being regenerated since a combustion "event" might spike the temperature to a range above 1100° C. and cause a phase change in the alumina, e.g., from gamma/eta phase into alpha phase alumina. A flowing stream of the oxidizing gas is desirable to allow heat transfer of the oxidation reaction into that flowing gas. Channelling of the gases should be avoided. The outlet temperature of the catalyst bed should be maintained at a temperature between 350° and 800° C., preferably between 450° and 700° C., and most preferably between 500° and 650° C. The exit may be monitored for the presence of carbon monoxide and carbon dioxide. As these disappear, the reaction products on the catalyst are also disappearing. When the oxidation step is complete, the catalyst component is again treated with one or more Lewis acids as specified above and returned to the alkylation step.

Prior to the higher temperature oxidation step, the catalyst may be stripped of volatile hydrocarbons and excess Lewis acid by heating the catalyst mass to a temperature of about 100° to 250° C., preferably 150° to 200° C. The resulting stream may be recycled to the alkylation step or its constituents separately recovered. Additionally, the removal of hydrocarbons and excess Lewis acid may be facilitated by contact with an inert gas such as helium, nitrogen, etc.

The alumina catalyst component may contain as much as 5% to 15% of thermal degradation products of the Lewis acid, e.g., $AlF_3$, and yet the catalyst system remains acceptably active.

The invention has been disclosed by direct description. Below may be found a number of examples showing various aspects of the invention. The examples are only examples of the invention and are not to be used to limit the scope of the invention in any way.

EXAMPLES

Example 1: Accelerated Catalyst Testing

This example shows the preparation of an alumina-based catalyst, its subsequent use in an alkylation reaction using model feeds, and the regeneration of that catalyst.

The alumina samples were dried at 110° C. overnight and charged to a continuous reactor having an internal volume of about 500 cc. The reactor temperature was controllable over the range of −5° C. to 40° C. For initial catalyst treatment, the reactor containing the catalyst was purged with an inert gas and cooled to about 0° C. About 275 cc of isobutane was added to the reactor. After a brief degassing, $BF_3$ was added batchwise. After $BF_3$ is added, the pressure typically drops as the alumina adsorbs or reacts with the $BF_3$. Additional infusions of $BF_3$ are made until the pressure in the reactor no longer drops. The $BF_3$ saturation equilibrium pressure was about 40 psig. The liquid phase concentration of $BF_3$ was about 1.5%. At that point the alumina had adsorbed or reacted with all of the $BF_3$ possible at that temperature and the catalyst was in its most active form.

A 4.5:1 mixture of isobutane/t-2-butene was then fed to the reactor at a rate which provided a continuous WHSV (gm olefin/gm $Al_2O_3$/hour) of 10. Samples were periodically removed from the reactor for analysis by gas-liquid chromatography. The RON were calculated from the gas-liquid chromatography data using the well-known correlations in Hutson and Logan, "Estimate Alky Yield and Quality", Hydrocarbon Processing, September, 1975, pp. 107-108.

At the end of each alkylation run the catalyst was regenerated according to the following procedure. Unreacted light hydrocarbons were vented from the reactor and the resulting mixture of spent $Al_2O_3$ and product alkylate were transferred to a 1.5 inch diameter quartz tube approximately three feet long having a medium frit in the midportion. The transfer was carried out under a nitrogen blanket to minimize exposure to atmospheric moisture. The spent catalyst was washed with 20 ml trimethylpentane per gram of catalyst and purged with dry nirogen. The isooctane wash is to reduce the quantity of heavy hydrocarbons removed during the calcination step.

The quartz tube containing spent catalyst was next fitted to an electric tube furnace and an upflow of 100 cc/min. of dry air was initiated through the bed. The catalyst was clearly seen to ebulate. Calcination was carried aout in two phases. In the first phase, light hydrocarbons were volatilixzed by heating the alumina catalyst to 150° C. in the flowing air for approximately 45 minutes. The second phase involved heating the catalyst to about 600° C. at a rate of about 15° C./minute and holding the catalyst at that temperature for two hours. The tube was then cooled and the regenerated catalyst transferred to a 110° C. drying oven for storage until the next alkylation test cycle.

The summary of the experiments and results is shown in Table 1 below. The results in the table show the hydrocarbon parameters after the catalyst has been regenerated.

TABLE 1

| Run Number | $C_8$ production (wt %) | RON + MON/2 |
| --- | --- | --- |
| new | 88.45 | 96.41 |
| 1 | 87.36 | 96.16 |
| 2 | 85.14 | 95.68 |
| 3 | 84.02 | 95.44 |
| 4 | 84.02 | 95.43 |

Figure 1B:
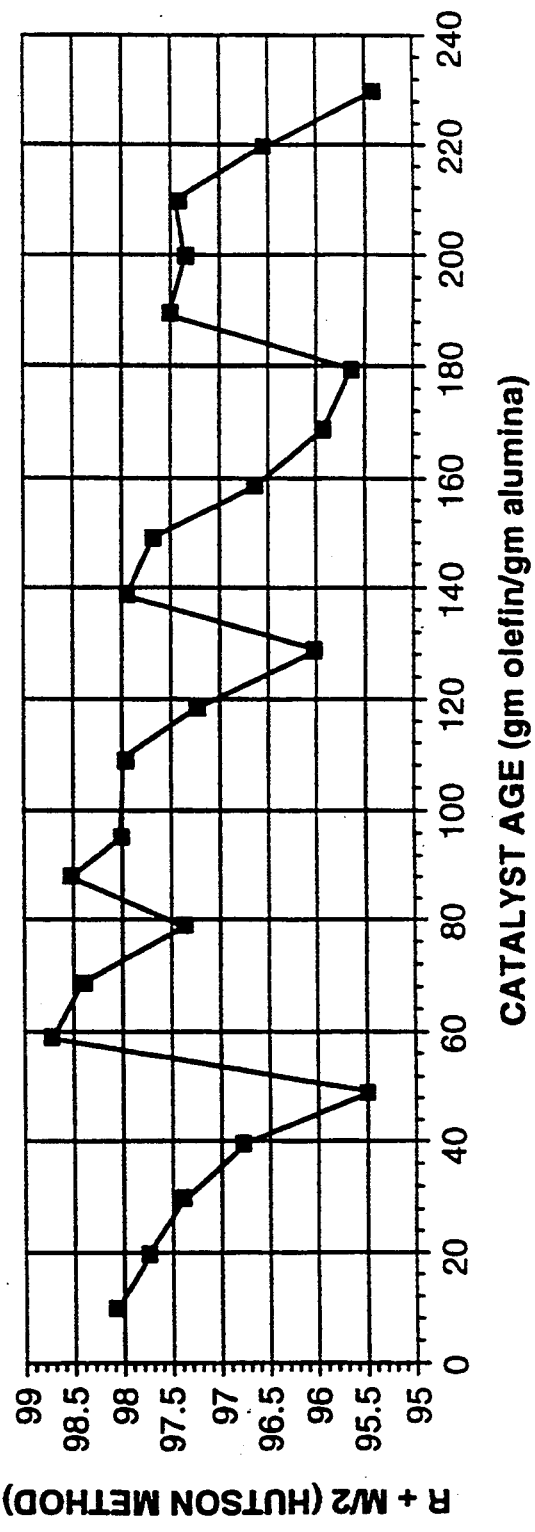

The results of that series of runs is shown in FIG. 1A ($C_8$ production) and FIG. 1B ((R+M)/2 of the resulting alkylate).

Example 2

This example shows the preparation of an alumina-based catalyst, its subsequent use in an alkylation reaction using a typical refinery feed, and the regeneration of that catalyst.

The alumina catalyst was dried at 110° C. overnight, then charged to a continous stirred tank alkylation reactor having an internal volume of 500 cc. The reactor was purged with dry nitrogen and cooled to 0° F. 280 cc of isobutane was then charged to the reactor and, under mechanical stirring of approximately 1600 rpm, the catalyst hydrocarbon mixture was alegassed to remove residual nitrogen. $BF_3$ was next added until saturation equilibrium was achieved at a total reactor pressure of 45 psig. This step completed the catalyst preparation phase and the catalyst was in its most active form. Mechanical stirring was maintained throughout the duration of the alkylation reaction.

The refinery feed used in this example was processed through a commercial MTBE unit and given a standard hydroisomerization treatment to reduce butadiene. The molar ratio of isobutane to olefin was 6:1. The olefin fraction composition was 86.7% 2-butene, 5.3% 1-butene, 3.8% isobutene, 01.1% propylene, and 4.1% mixed amylenes. The isoparaffin/olefin mixture was fed to the reactor at a rate which provided a WHSV (gm olefin/gm catalyst/hour) of 4.0. The reactor liquid level was maintained at 280 cc by a process of continuous product removal. Fresh $BF_3$ was added to the reactor to replace the amount withdrawn in the liquid product. The $BF_3$ concentration in this product was approximately 1.5% by weight. Product samples were withdrawn periodically from the reactor for analysis by gas-liquid chromatography. Research octane and motor octane numbers were determined by the correlations in Hutson and Logan, "Estimating Alky Yield and Quality", Hydrocarbon Processing, September, 1975, pp. 107-108.

At the end of each alkylation run the catalyst was regenerated by the following procedure. Unreacted light hydrocarbons and $BF_3$ were vented from the reactor and the remaining mixture of spent catalyst and product alkylate were transferred to a three foot long by 1.5 inch diameter quartz tube which had a medium quartz frit in the center. The catalyst was washed by suction filtration with approximately 20 ml fresh isooctane/gram spend catalyst. This served to reduce the level of heavy hydrocarbon removed in the subsequent calcination step.

The quartz tube containing the spent catalyst was fitted to an electric furnace and an up flow of dry air was initiated through the bed. The air flow was adjusted until the bed was seen to ebulate. The flow required for this was approximately 150 cc/min. Calcination was carried out in two phases. In the first phase, light hydrocarbons were volatilized by heating the spent catalyst to 150° C. and holding for 45 minutes. In the second phase, the bed was heated to a final temperature of 600° C. at a rate of 15° C./minute and held for one hour. The tube was finally cooled and the regeneration catalyst was transferred to a 110° C. drying oven for storage until the next reaction cycle.

The results of the series of runs and regenerations is shown in FIG. 2A ($C_8$ production) and 2B ((R+M)/2 of the resulting alkylate).

It should be clear that one having ordinary skill in this art would envision equivalents to the processes found in the claims that follow and that those equivalents would be within the scope and spirit of the claimed invention.

We claim as our invention:

1. A method for regenerating an alkylation catalyst component which component comprises transition alumina which has been contacted with a strong Lewis acid to produce an alkylation catalyst component containing between 0.5% and 30% by weight of Lewis acid and has been partially deactivated by use in an alkylation reaction medium, comprising the steps of:
   a. separating the alkylation catalyst component from the alkylation reaction medium,
   b. stripping light hydrocarbons and excess Lewis acid from the alkylation catalyst component using an inert gas,
   c. heating the alkylation catalyst component to a temperature of 100° to 250° C.,
   d. contacting the alkylation catalyst component with an oxygen-containing gas and maintaining a gas outlet temperature between 350° and 800° C. to regenerate the alkylation catalyst component comprising transition alumina.

2. The process of claim 1 where the transition alumina is selected from gamma-alumina, eta-alumina, theta-alumina, chi-alumina, kappa-alumina, lambda-alumina, rho-alumina, and mixtures.

3. The process of claim 2 where the transition alumina is selected from gamma-alumina, eta-alumina, and mixtures.

4. The process of claim 1 where the strong Lewis acid is selected from $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FeCl_3$, and $FeBr_3$.

5. The process of claim 1 where the strong Lewis acid is selected from $SbF_5$, $AlCl_3$, and $BF_3$.

6. The process of claim 5 where the strong Lewis acid is $BF_3$.

7. The process of claim 1 where the temperature is maintained between 450° and 700° C.

8. The process of claim 7 where the temperature is maintained between 500° and 650° C.

9. An alkylation process comprising the steps of:
   a. contacting a mixture comprising isoparaffins and n-olefins with an acidic alkylation catalyst system comprising transition alumina which has been previously contacted with a Lewis acid under alkylation conditions to produce an alkylate stream,
   b. separating the alkylate stream from the acidic transition alumina based alkylation catalyst,
   c. stripping light hydrocarbons and excess Lewis acid from the alkylation catalyst component using an inert gas,
   d. heating the alkylation catalyst component to a temperature of 100° to 250° C.,
   e. contacting the acidic transition alumina based alkylation catalyst with an oxygen-containing gas and maintaining a gas outlet temperature between 350° and 800° C. to regenerate that catalyst, and
   f. recycling the regenerated alkylation catalyst to the alkylation step.

10. The process of claim 9 where the transition alumina is selected from gamma-alumina, eta-alumina, theta-alumina, chi-alumina, kappa-alumina, lambda-alumina, rho-alumina, and mixtures.

11. The process of claim 10 where the transition alumina is selected from gamma-alumina, eta-alumina, and mixtures.

12. The process system of claim 9 where the strong Lewis acid is selected from $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FeCl_3$, and $FeBr_3$.

13. The process system of claim 9 where the strong Lewis acid is selected from $SbF_5$, $AlCl_3$, and $BF_3$.

14. The process system of claim 13 where the strong Lewis acid is $BF_3$.

15. The process of claim 9 where the temperature is maintained between 450° and 650° C.

16. The process of claim 15 where the temperature is maintained between 500° and 650° C.

17. The process of claim 9 where alkylation conditions include a temperature in the range of −30° C. to 50° C.

18. The process of claim 9 where the mixture comprises 2-butene and isoparaffin.

19. The process of claim 9 including the step of mixing the alkylate stream with other hydrocarbons to produce a gasoline blending component or gasoline.

20. The process of claim 1 additionally comprising the step of recycling light hydrocarbons and Lewis acid to the alkylation catalyst component.

21. The process of claim 9 additionally comprising the step of recycling light hydrocarbons and Lewis acid to the alkylation catalyst component.

* * * * *